(12) United States Patent
Brandt et al.

(10) Patent No.: US 7,759,346 B2
(45) Date of Patent: Jul. 20, 2010

(54) [[2-(AMINO-3,4-DIOXO-1-CYCLOBUTEN-1-YL)AMINO]ALKYL]-ACID DERIVATIVES FOR THE TREATMENT OF PAIN

(75) Inventors: Michael Richard Brandt, Flemington, NJ (US); Margaret Maria Zaleska, Narberth, PA (US); John Allen Moyer, New Hope, PA (US)

(73) Assignee: Wyeth LLC, Madison, NJ (US)

( * ) Notice: Subject to any disclaimer, the term of this patent is extended or adjusted under 35 U.S.C. 154(b) by 890 days.

(21) Appl. No.: 11/433,737

(22) Filed: May 12, 2006

(65) Prior Publication Data

US 2006/0205696 A1 Sep. 14, 2006

Related U.S. Application Data

(62) Division of application No. 10/267,159, filed on Oct. 9, 2002, now Pat. No. 7,098,200.

(60) Provisional application No. 60/328,245, filed on Oct. 10, 2001.

(51) Int. Cl.
*A01N 57/00* (2006.01)
*A01N 43/62* (2006.01)
*A61K 31/69* (2006.01)
*C07D 243/12* (2006.01)

(52) U.S. Cl. .................. 514/249; 514/75; 514/221; 540/517

(58) Field of Classification Search .................. 514/75, 514/221, 249; 540/500, 517
See application file for complete search history.

(56) References Cited

U.S. PATENT DOCUMENTS

| | | | |
|---|---|---|---|
| 5,124,319 A | 6/1992 | Baudy | 514/80 |
| 5,168,103 A | 12/1992 | Kinney et al. | 514/221 |
| 5,240,946 A | 8/1993 | Kinney et al. | 514/364 |
| 5,990,307 A | 11/1999 | Asselin et al. | 540/542 |
| 6,011,168 A | 1/2000 | Asselin et al. | 558/172 |
| 6,451,848 B1 | 9/2002 | Behl et al. | 514/468 |
| 2004/0082543 A1 | 4/2004 | Cheung | 514/80 |

FOREIGN PATENT DOCUMENTS

| | | |
|---|---|---|
| EP | 0 496 561 A2 | 7/1992 |
| EP | 0 778 023 A1 | 6/1997 |
| EP | 0 994 107 A1 | 4/2000 |
| WO | 98/15542 A1 | 4/1998 |
| WO | 99/06417 A1 | 2/1999 |
| WO | 99/64041 A1 | 12/1999 |
| WO | 03/065982 A2 | 8/2003 |
| WO | 2004/039371 A2 | 5/2004 |

OTHER PUBLICATIONS

Abou-Gharbia, Abstract Paper, *Am. Chem. Soc.*, 221$^{st}$ MEDI 202 (2001).
Abrahams et al., *Emerging Drugs*, 5(4), 385-413 (2000).
Baron et al., *Psychopharmacology*, 118, 42-51 (1995).
Baudy et al., *J. Med. Chem.* 36, 331-342 (1993).
Baudy et al., *J. Med. Chem.* 44,1516-1529 (2001).
Bennett, Gary et al., *Pain*, 33, 87-107 (1988).
Bennett, *Journal of Pain & Symptom Management*, 19(1 Suppl.), S2-S6 (2000).
Boyce, S. et al. *Neuropharmacology*, 38, 611-623 (1999).
Bradford et al., *Stroke & Cerebral Circulation*, Abstract (1998).
Brandt et al., *Pharmacology & Experimental Therapeutics*, 296(3), 939-946 (2001).
Brandt, M. "Efficacy of Novel NMDA Receptor Antagonists," Presented at *Advancing Preclinical and Clinical Applications of Pain Therapeutics* in San Diego, CA, Oct. 28-29, 2004.
Brandt, M. et al., Abstract, "NMDA antagonist for the treatment of diabetic neuropathy," Presented at the *SMI Pain Conference* in London, Jun. 9, 2004.
Brandt; M. et al., "Antiallodynic and antihyperalgesic effects of the NMDA receptor antagonist perzinfotel (EAA-090) in neuropathic pain models," Presented at *Advancing Preclinical and Clinical Applications of Pain Therapeutics* in San Diego, CA, Oct. 28-29, 2004.
Bullock, "Opportunities for Neuroprotective Drugs in Clinical Management of Head Injury," *The Journal of Emergency Medicine*, vol. 11, pp. 23-30, 1993.
Chaplan et al., *Pharmacology & Experimental Therapeutics*, 280(2), 829-838 (1997).
Chaplan, S.R., *Journal of Neuroscience Methods*, 53, 55-63 (1994).
Childers et al., *Drugs of the Future*, 27(7), 633-638 (2002).

(Continued)

*Primary Examiner*—James O. Wilson
*Assistant Examiner*—Paul V. Ward
(74) *Attorney, Agent, or Firm*—Joel B. Silver

(57) ABSTRACT

This invention provides a method of treating pain in a mammal that includes administering to a mammal in need of such treatment a pain treating effective amount of a compound of the formula (I):

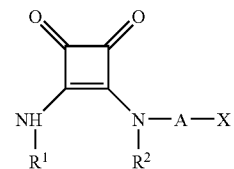

where $R^1$ is H, alkyl or phenylalkyl; $R^2$ is H, alkyl, alkenyl or phenylalkyl; or $R^1$ and $R^2$ taken together as Z are —CH$_2$CH$_2$—, —CH$_2$C(R$^6$)(R$^7$)CH$_2$— or —CH$_2$C(R$^8$)(R$^9$)—C(R$^{10}$)(R$^{11}$)CH$_2$—, where $R^6$, $R^8$ and $R^{10}$ are, independently, H, alkyl or hydroxyl and $R^7$, $R^9$ and $R^{11}$ are, independently, H or alkyl; A is alkylene or alkenylene; X is CO$_2$R$^3$, P(O)(OR$^4$)(OR$^5$), 3,5-dioxo-1,2,4-oxadiazolidin-2-yl or 5-tetrazolyl in which $R^3$, $R^4$ and $R^5$ are, independently, H or alkyl, or a pharmaceutically acceptable salt thereof. The present invention also provides pharmaceutical compositions for treating pain containing a pain treating effective amount of the compound of formula (I).

6 Claims, No Drawings

OTHER PUBLICATIONS

Chizh, B. et al., *TRENDS in Pharmacological Sciences*, 22(12), 636-642 (2001).
Fix et al., *Experimental Neurology*, 123, 204-215 (1998).
France et al., *European Journal of Pharmacology*, 159, 133-139 (1989).
France et al., *Journal of Pharmacology & Experimental Therapeutics*, 257(2), 727-734 (1991).
Gilron et al, "A randomized, controlled trial of high-dose dextromethorphan in facial neuralgias" *Neurology*, vol. 55, pp. 964-971 (Oct. 2000).
Hao et al., *Pain*, 66, 279-285 (1996).
*Harrison's Principles Of Internal Medicine*, 13th Ed., Edited by Isselbacher et al, pp. 2320-2328, © 1994 McGraw-Hill, Inc.
Herrling, P.L., Academic Press, Chapter 1, 1-6 (1997).
Hewitt, David, *The Clinical Journal of Pain*, 16, S73-S79 (2000).
Hussain, A., *Advanced Drug Delivery Reviews*, 29, 39-49 (1998).
Karlsten et al., *Drug & Aging*, 11(5), 398-412 (1997).
Kinney et al., *J. Med. Chem.*, 41, 236-246 (1998).
Kristensen, et al., Database Biosis, Biosciences Information Service, Abstract XP002228851.
Kristensen, et al., *Pain.* 51, 249-253 (1992).
Marion, D. W. et al., *The New England Journal of Medicine*, 336(8), 540-546 (1997).
McRoberts et al., *Gastroenterology*, 120(7), 1737-1748 (2001).
Menniti, F. et al, *European Journal of Pharmacology*, 331, 117-126 (1997).
Millan et al., *Neuroscience Letters*, 178, 139-143 (1994).
Mori et al., *Behavioral Brain Research*, 119, 33-40 (2001).
Mosconi et al., *Pain*, 64, 37-57 (1996).
Mutel, V. et al., *Journal of Neurochemistry*, 70, 2147-2155 (1998).
Nicholson et al., *Behavioural Pharmacology*, 9, 231-243 (1998).
Olivar et al., *Pain*, 79, 67-73 (1999).
Olney et al., *Science*, 254, 1515-1518 (1991).
Olney, et al., *Science*, 244, 1360-1362 (1989).
Pal et al., *Burns*, 23(5), 404-412 (1997).
Parsons, C., *European Journal of Pharmacology*, 429, 71-78 (2001).
Radanov et al, "Symptomatic approach to posttraumatic headache and its possible implicatons for treatment" *European Spine Journal*, vol. 10, pp. 403-407 (Jun. 16, 2001).
Rogawski et al., *Trends in Pharmaceutical Sciences*, 14, 325-331 (1993).
Rogers, K. et al., "Effects of the NMDA receptor antagonist perzinfotel (EAA-090) on chemically-induced thermal hypersensitivity," Presented at *Advancing Preclinical and Clinical Applications of Pain Therapeutics* in San Diego, CA, Oct. 28-29, 2004.
Rundek, T. et al., *Acta Clin*. Croat 41, 45-49 (2002).
Rygh et al., *Pain*, 93, 15-21 (2001).
Sang, *Journal of Pain & Symptom Management*, 19(1 Suppl.), S21-S25 (2000).
Sun, L. et al., *The Journal of Pharmacology & Experimental Therapeutics*, 310(2), 563-570 (2004).
Suzuki et al., *Pain*, 91, 101-109 (2001).
Swahn, B. M. et al., *Bioorganic & Medicinal Chemistry Letters*, 6(14), 1635-1640 (1996).
Tang et al., *Nature*, 401, 63-69 (1999).
Wei et al., *Nature*, 4(2), 164-169 (2001).
Wiesenfeld-Hallin, Z., "Combined Opioid-NMDA Antagonist Therapies," Drugs, 1998, 55(1), 1-4.
Woolf, et al., *Pain*, 44, 293-299 (1991).
Yamamoto, T., "N-methyl-D-aspartate (NMDA) receptor and pain," *Masui*, Nov. 1996, 45(11), 1312-1318 [English abstract only].

[[2-(AMINO-3,4-DIOXO-1-CYCLOBUTEN-1-YL)AMINO]ALKYL]-ACID DERIVATIVES FOR THE TREATMENT OF PAIN

CROSS-REFERENCE TO RELATED APPLICATIONS

This application is a divisional application of U.S. application Ser. No. 10/267,159 filed Oct. 9, 2002 now allowed, which claims the benefit of U.S. Application Ser. No. 60/328,245 filed Oct. 10, 2001, which are hereby incorporated by reference in their entirety.

BACKGROUND OF THE INVENTION

Pain has been characterized and described in various different ways in the literature. For example, pain can be intense, localized, sharp or stinging, and/or dull, aching, diffuse or burning in nature. Pain can also be centralized, taking place in the dorsal horn of the spinal cord, the brain stem and brain, or peripheral, taking place at the injury site and surrounding tissue. Pain that occurs for extended periods of time (i.e., persistent) is generally referred to as chronic pain. Examples of chronic pain include neuropathic pain, inflammatory pain, and cancer pain. These pains can be related to hyperalgesia and/or allodynia, where hyperalgesia refers to an increase in sensitivity to a typically noxious stimulus and allodynia refers to an increase in sensitivity to a typically non-noxious stimulus.

A type of chronic pain that currently lacks adequate pharmacological treatment is neuropathic pain. Neuropathic pain is generally thought of as a chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or excitatory functions and abnormal interactions between the parasympathetic and sympathetic nervous systems. A wide range of clinical conditions may be associated with or form the basis for neuropathic pain including for example diabetes, post traumatic pain of amputation, lower back pain, cancer, chemical injury or toxins, other major surgeries, peripheral nerve damage due to traumatic injury compression, nutritional deficiencies, or infections such as shingles or HIV.

There are various types of agents currently being used to treat pain such as for example, non-narcotic analgesics such as aspirin, acetaminophen or ibuprofen; non-steroidal anti-inflammatory drugs (NSAID); narcotic analgesics such as morphine, hydromorphone, fentanyl, codeine or meperidine; steroids such as prednisone or dexamethasone; tricyclic antidepressants such as amitriptyline, desipramine, or imipramine; antiepileptics such as gabapentin, carbamazepine, topiramate, sodium valproate or phenyloin; or combinations of these different agents. However, these agents are typically unsatisfactory for treating pain of a chronic nature, and can have adverse effects such as drowsiness, dizziness, dry mouth, weight gain, memory impairment, and/or orthostatic hypotension.

Of more recent interest has been the use of inhibitors of the N-methyl-D-aspartate ("NMDA") receptors to treat pain (hereinafter called "NMDA receptor antagonists"). It has been shown that NMDA receptors are involved in a wide range of processes including, neuronal death following ischemia, synaptic plasticity associated with memory formation and central sensitization during persistent pain. It is believed that glutamate, which regulates NMDA receptors, plays a key role in pain and especially chronic pain.

NMDA receptors are localized throughout the central nervous system. NMDA receptors are ligand-gated cation channels that modulate sodium, potassium and calcium ions flux when they are activated by glutamate in combination with glycine. Structurally, the NMDA receptor is thought to be comprised of heteromultimeric channels containing two major subunits designated as NR1 and NR2. These subunits contain a glycine binding site, a glutamate binding site and polyamine binding site. For the NR1 subunit, multiple splice variants have been identified, whereas for the NR2 subunit, four individual subunit types (NR2A, NR2B, NR2C, and NR2D) have been identified. The NMDA receptor also contains a $Mg^{++}$ binding site located inside the pore of the ionophore of the NMDA receptor/channel complex, which blocks the flow of ions. Phencyclidine, as well as other compounds, appear to bind to this $Mg^{++}$ site. In order for PCP to gain access to the PCP receptor, the channel must first be opened by glutamate and glycine (i.e., use dependence).

Various NMDA antagonists have been developed to interact with these sites of the NMDA receptor. For example, NMDA receptor glutamate site antagonists refer to those antagonists that interact with the glutamate binding site of the NR2 subunit. Examples of NMDA receptor glutamate site antagonists that have been shown in preclinical models to suppress pain include CGS-19755 (Selfotel; cis-4-phosphonomethyl-2-piperidine carboxylic acid), CPP (3-(2-carboxypiperazinyl-4-yl)propyl-1-phosphonic acid) and AP5 (D-2 amino 5-phosphonopentanoic acid). See e.g., Karlsten and Gordh, *Drugs and Aging* 11: 398-412, (1997). Other NMDA receptor antagonists have been identified that interact at the strychinine-in-sensitive glycine site ($glycine_B$) such as L701324 (7-chloro-4-hydroxy-3-(3-phenoxy)phenyl-2(1H)-quinoline) and at the polyamine site such as ifenprodil. Non-competitive NMDA receptor channel blocking antagonists that have been found effective in suppressing pain include dextromethorphan, ketamine, memantine, and amantadine. See e.g., Hao et al., *Pain* 66:279-285 (1996); Chaplan et al., *J. Pharmacol. Exper. Ther.* 280:829-838 (1997); Suzuki et al., *Pain* 91:101-109, (2000); Bennett, *J. Pain Symptom Management* 19: S2 (2000); Sang, *J. Pain Symp. Manag.* 19 (1): S21, (2000).

NMDA receptor antagonists have been used in clinical settings to treat pain. For example, ketamine has been used to treat postherpetic neuralgia pain, phantom limb pain, post nerve injury pain, postoperative pain, and burn pain. Also, for example dextromethorphan has been used to treat diabetic neuropathy pain, and postoperative pain; and amantadine has been used to treat pain in cancer patients.

Clinical usefulness of these NMDA receptor antagonists have been limited by adverse effects such as headache, disturbances of motor function such as ataxia, sedation and/or psychotomimetic effects such as dizziness, hallucinations, dysphoria, or disturbances of cognitive function at analgesic doses. See e.g., Hao et al., *Pain* 66:279-285 (1996); Chaplan et al., *J. Pharmacol. Exper. Ther.* 280:829-838 (1997); Suzuki et al., *Pain* 91:101-109, (2000); Bennett, *J. Pain Symptom Management* 19: S2 (2000); Sang, *J. Pain Symp. Manag.* 19 (1): S21, (2000). For example, the high affinity NMDA receptor channel blocker ketamine, which is occasionally used for burn related pain has reported adverse effects that has limited its use in patients (Pal et al., *Burns* 23: 404-412, 1997). Additionally, development of the NMDA receptor channel blocking antagonist dizocilpine (MK-801) was terminated because of psychotomimetic effects similar to those produced by phencyclidine (i.e., PCP). It has been suggested that lower affinity channel blockers such as dextromethorphan, amantadine and memantine might have fewer adverse effects than the high affinity blockers (Rogawski, *Trends Pharmacol. Sci.* 14:325, 1998). In support of this view, dextromethorphan had analgesic effects in patients suffering from diabetic neuropathy with fewer side effects than ketamine (Sang, *J. Pain Symp. Manag.* 19 (1): S21, 2000). Similarly, amantadine relieved surgical neuropathic pain in cancer patients with fewer side effects (Hewitt, *Clin. J. Pain* 16: 573, 2000).

However, even with the lower affinity noncompetitve NMDA receptor channel blocking antagonists, like the higher affinity noncompetitive antagonists, there have been undesirable psychotomimetic effects which have hampered development. For example, in preclinical models, NMDA receptor channel blockers of varying affinities consistently produce PCP-like discriminative stimulus effects in rats trained to discriminate between saline and PCP. Memantine, ketamine and dizocilpine all substitute for the PCP-like discriminative stimulus effects in rats (Nicholson et al., *Behav. Pharmacol.* 9(3): 231-243, 1998; Mori et al., *Behav. Brain Res.* 119:33-40, 2001). Moreover, like PCP, memantine maintains self-administration in monkeys suggesting that it might have abuse potential in humans (Nicholson et al., *Behav. Pharmacol.* 9(3): 231-243, 1998). Use dependent NMDA receptor channel blockers can also increase heart rate and blood pressure, which can further limit their clinical utility.

Although NMDA receptor glutamate antagonists do not have the degree of psychotomimetic side effects in humans or PCP-like discriminative stimulus effects in non-humans (see e.g., Baron and Woods, *Psychopharmacol.* 118(1): 42-51, (1995); Mori et al., *Behav. Brain Res.* 119:33-40, (2001); France et al., *J. Pharmacol. Exper. Ther.* 257(2): 727-734, (1991); France et al., *Eur. J. Pharmacol.* 159(2): 133-139, (1989)), they have been shown to have many undesirable side effects. For example, the NMDA glutamate antagonist CGS-19755 has been shown to have a transient, reversible induction of vacuoles in some layers of the cingulate and retrosplenial cortices of mice and rats at behaviorly effective doses (i.e., effectiveness/vacuolization ratio of 1). See e.g., Herring et al., *Excitatory Amino Acids Clinical Results with Antagonists*, published by Academic Press, Chptr 1 (1997). Although the functional implications of vacuolization are unclear, previous studies suggest that this vacuolization correlates with the psychotomimetic effects produced by NMDA receptor antagonists (see e.g., Olney et al., *Science*, 244: 1630-1632, 1989; Olney et al., *Science* 254: 1515-1518, 1991) and might lead to limited neuronal cell death as in the case of dizocilpine (Fix et al., *Exp. Neurol.* 123: 204-215, 1993).

Thus, it would be desirable to find alternative compounds effective in treating pain. Preferably these compounds would have reduced adverse side effects and/or be more effective in treating pain.

U.S. Pat. No. 5,168,103 to Kinney et al. (hereinafter "Kinney") discloses certain [[2-(Amino-3,4-dioxo-1-cyclobuten-1-yl)amino]alkyl]-acid derivatives useful as neuroprotectant and anticonvulsant agents. These [[2-(Amino-3,4-dioxo-1-cyclobuten-1-yl)amino]alkyl]-acid derivatives are disclosed as competitive NMDA antagonists useful to treat certain central nervous system disorders such as convulsions, brain cell damage and related neurodegenerative disorders.

Side effects of one of the compounds disclosed in the Kinney patent, [2-(8,9-dioxo-2,6-diazabicyclo[5.2.0]non-1(7-en-2-yl)ethyl]phosphonic acid, were previously evaluated in healthy volunteers in a phase I study conducted in Europe. This study was in connection with developing this compound for treating stroke-related ischemia in patients (Bradford et al., *Stroke and Cerebral Circulation* abstract, 1998).

The present inventors have found that the cyclobutene derivatives in Kinney are effective in treating pain in a variety of preclinical pain models. For example, the present inventors have found that these cyclobutene derivatives can relieve pain under conditions where comparitor NMDA receptor antagonists tested herein do not. Additionally, these cyclobutene derivatives surprisingly do not have the degree of adverse side effects exhibited by known NMDA receptor antagonists at dosages needed for pain relief.

For example, the present inventors, as described in more detail hereinafter, have found that compounds disclosed in Kinney, such as [2-(8,9-dioxo-2,6-diazabicyclo[5.2.0]non-1(7-en-2-yl)ethyl]phosphonic acid, did not produce ataxia or sedation in comparison to other reported competitive glutamate antagonists (CGS-19755), competitive polyamine antagonists (ifenprodil) and use dependent channel blockers (MK-801, memantine; dizocilipine, ketamine) at doses needed to relieve pain in preclinical models. Additionally, as mentioned previously, some NMDA receptor antagonists, such as CGS-19755 were found to exhibit a transient, reversible induction of vacuoles in some layers of the cingulate and retrosplenial cortices of mice and rats. In contrast to CGS-19755, which caused vacuolization at behaviorally effective doses, cyclobutene derivatives such as [2-(8,9-dioxo-2,6-diazabicyclo[5.2.0]non-1(7-en-2-yl)ethyl]phosphonic acid had an effectiveness/vacuolization ratio as large as 16. Moreover, unlike the NMDA receptor channel blocking antagonists previously mentioned herein, the cyclobutene derivatives such as [2-(8,9-dioxo-2,6-diazabicyclo[5.2.0]non-1(7-en-2-yl) ethyl]phosphonic acid did not substitute for PCP in rats, suggesting that this compound would not be associated with PCP-like psychotomimetic effects or contain PCP-like abuse liability. Additionally, [2-(8,9-dioxo-2,6-diazabicyclo[5.2.0]non-1(7-en-2-yl)ethyl]phosphonic acid was devoid of many PCP-like effects up to doses 4-10 times higher than those effective in an ischemia model.

SUMMARY OF INVENTION

The present invention provides a method of treating pain in a mammal that includes administering to a mammal in need of such treatment a pain treating effective amount of at least one compound having the formula (I):

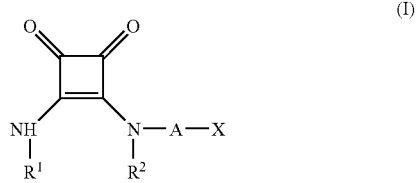

where:

$R^1$ is hydrogen, alkyl of 1 to 6 carbon atoms or phenylalkyl of 7 to 12 carbon atoms;

$R^2$ is hydrogen, alkyl of 1 to 6 carbon atoms, alkenyl of 2 to 6 carbon atoms or phenylalkyl of 7 to 12 carbon atoms; or $R^1$ and $R^2$ taken together are Z, which is —CH$_2$CH$_2$—, —CH$_2$C(R$^6$)(R$^7$)CH$_2$— or —CH$_2$C(R$^8$)(R$^9$)—C(R$^{10}$)(R$^{11}$)CH$_2$—, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms;

A is alkylene of 1 to 6 carbon atoms or alkenylene of 2 to 6 carbon atoms;

X is $CO_2R^3$, $P(O)(OR^4)(OR^5)$, 3,5-dioxo-1,2,4-oxadiazolidin-2-yl or 5-tetrazolyl where $R^3$, $R^4$ and $R^5$ are, independently, hydrogen or alkyl of 1 to 6 carbon atoms;

or a pharmaceutically acceptable salt thereof.

The present invention also provides a pharmaceutical composition that contains: a pain treating effective amount of the compound of formula (I) or a pharmaceutically acceptable salt thereof, where $R^1$ and $R^2$ taken together are Z and the remaining variables are defined as before; and at least one pharmaceutical carrier. In a preferred embodiment, this composition also contains a pharmaceutically effective amount of at least one pain relieving agent. Also provided is a pharmaceutical composition that contains a pain treating effective amount of the compound of formula (I) or a pharmaceutically acceptable salt thereof, and a pharmaceutically effective amount of at least one pain relieving agent.

The present invention also provides a pharmaceutical composition in unit dosage form and a therapeutic package containing the compound of formula (I) in unit dosage form for treating pain in a mammal.

DETAILED DESCRIPTION OF THE INVENTION

Compounds useful in the present invention for treating pain include cyclobutene derivatives of formula (I)

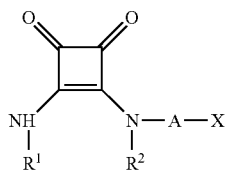

(I)

where
$R^1$ is hydrogen, alkyl of 1 to 6 carbon atoms or phenylalkyl of 7 to 12 carbon atoms;

$R^2$ is hydrogen, alkyl of 1 to 6 carbon atoms, alkenyl of 2 to 6 carbon atoms or phenylalkyl of 7 to 12 carbon atoms; or $R^1$ and $R^2$ taken together are Z, which is $-CH_2CH_2-$, $-CH_2C(R^6)(R^7)CH_2-$ or $-CH_2C(R^8)(R^9)-C(R^{10})(R^{11})CH_2-$, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms;

A is alkylene of 1 to 6 carbon atoms or alkenylene of 2 to 6 carbon atoms;

X is $CO_2R^3$, $P(O)(OR^4)(OR^5)$, 3,5-dioxo-1,2,4-oxadiazolidin-2-yl or 5-tetrazolyl in which $R^3$, $R^4$ and $R^5$ are, independently, hydrogen or an alkyl of 1 to 6 carbon atoms;

or a pharmaceutically acceptable salt thereof.

Examples of alkyl for $R^{1-11}$ and alkylene for A are straight or branched groups such as methyl, ethyl, propyl (e.g., n-propyl, isopropyl), butyl (e.g., n-butyl, isobutyl), pentyl (e.g., n-pentyl, isopentyl) or hexyl. Preferred alkyl groups of the present invention have 1 to 4 carbon atoms. Examples of alkenyl for R and alkenylene for A are straight or branched mono-, di-, or polyunsaturated groups such as vinyl, prop-1-enyl, allyl, methallyl, but-1-enyl, but-2-enyl or but-3-enyl.

Examples of phenylalkyl groups for $R^1$ and $R^2$ are such groups wherein the alkyl moiety is a straight or branched carbon chain having 1 to 6 carbon atoms such as benzyl, phenylethyl, 3-phenylpropyl, or 4-phenyl butyl.

Preferred values for $R^1$ and $R^2$ are, independently, hydrogen, methyl, ethyl, allyl, methallyl or benzyl.

Other preferred values are when $R^1$ and $R^2$ are taken together to form a moiety Z in the formula (II):

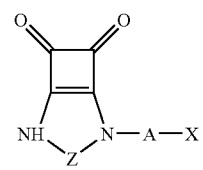

(II)

where Z is $-CH_2CH_2-$, $-CH_2C(R^6)(R^7)CH_2-$, or $-CH_2C(R^8)(R^9)-C(R^{10})(R^{11})CH_2-$, and preferably $-CH_2C(R^6)(R^7)CH_2-$, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms. Preferably, $R^6$ to $R^{11}$ are hydrogen.

With respect to A, preferred examples of alkylene groups are straight or branched chain groups having 1 to 4 carbon atoms such as: $-CH_2-$, $-CH_2CH_2-$, $-CH(CH_3)CH_2-$, $-CH_2CH(CH_3)-$, $-(CH_2)_3-$, or $-(CH_2)_4-$. Preferred examples of alkenylene groups for A are cis or trans groups preferably having 2 to 4 carbon atoms such as $-CH_2-CH=CH-$, $-CH=C(CH_3)-$, $-C(CH_3)=CH-$, $-CH=CH-CH_2-$, $-CH_2-CH=CH-CH_2-$ or $-CH_2-CH=C(CH_3)-$. Preferably A is alkylene of 1 to 4 carbon atoms or trans-2-butylene. Preferred substituents for X are carboxyl, phosphonyl or 5-tetrazolyl.

In a most preferred embodiment of the present invention, the compounds useful in the present invention have the formula (III):

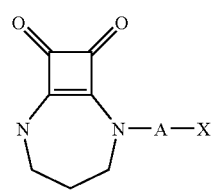

(III)

where A and X are defined as before.

The compounds useful in the present invention also include pharmaceutically acceptable salts of the compounds of formula (I). By "pharmaceutically acceptable salt", it is meant any compound formed by the addition of a pharmaceutically acceptable base or acid and a compound of formula (I) to form the corresponding salt. By the term "pharmaceutically acceptable" it is meant a substance that is acceptable for use in pharmaceutical applications from a toxicological perspective and does not adversely interact with the active ingredient. Preferably, the pharmaceutically acceptable salts are alkali metal (sodium, potassium, lithium) or alkaline earth metal (calcium, magnesium) salts of the compounds of formula (I), or salts of the compounds of formula (I) with pharmaceutically acceptable cations derived from ammonia or a basic amine. Examples of the later include, but are not limited to, ammonium, mono-, di-, or trimethylammonium, mono-, di-, or triethylammonium, mono-, di-, or tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 1-isopropylpyrrolidinium, 1,4-dimethylpiperazinium, 1-n-butylpiperidinium, 2-methylpiperidinium, 1-ethyl-2-methylpiperidinium, mono-, di-, or triethanolammonium, tris-(hydroxymethyl)methylammonium, or phenylmonoethanolammonium.

The compounds described herein can be prepared by the methods described in U.S. Pat. No. 5,168,103 (Kinney et al.), issued Dec. 1, 1992, the entire contents of which are incorporated herein by reference. Compounds of this invention can also be prepared by the methods described in U.S. Pat. No. 5,240,946 (Kinney et al.), U.S. Pat. No. 5,990,307 (Asselin et al.), or U.S. Pat. No. 6,011,168 (Asselin et al.); the contents of these patents are also entirely incorporated herein by reference.

Preferred compounds useful in the present invention include the following compounds or their pharmaceutically acceptable salts:

N-(2-Amino-3,4,dioxo-1-cyclobuten-1-yl)beta-alanine;
2-[2-[(2-Amino-3,4-dioxo-1-cyclobuten-1-yl)amino]ethyl]-1,2,4-oxadiazolidine-3,5-dione;
N-(2-Amino-3,4-dioxo-1-cyclobuten-1-yl)-N-(2-propenyl)glycine;
[2-[(2-Amino-3,4-dioxo-1-cyclobuten-1-yl)amino]ethyl]phosphonic acid;
[(E)-4-[(2-Amino-3,4-dioxo-1-cyclobuten-1-yl)amino]-2-butenyl]phosphonic acid;
[2-[(2-Amino-3,4-dioxo-1-cyclobuten-1-yl)methylamino]ethyl]phosphonic acid;
[2-(7,8-Dioxo-2,5-diazabicyclo[4.2.0]oct-1(6)-en-2-yl)ethyl]phosphonic acid;
[2-(8,9-Dioxo-2,6-diazabicyclo[5.2.0]non-1(7)-en-2-yl)ethyl]phosphonic acid;
[2-(4-Hydroxy-8,9-dioxo-2,6-diazabicyclo[5.2.0]non-1(7)en-2-yl)ethyl]phosphonic acid;
8,9-Dixo-2,6-diazabicyclo[5.2.0]non-1(7)-ene-2-acetic acid; 2-[(1H-Tetrazol-5-yl)methyl]-2,6-diazabicyclo[5.2.0]-non-1-(7)-ene-8,9-dione; or
[2-(9,10-Dioxo-2,7-diazabicyclo[6.2.0]dec-1(8)-en-2-yl)ethyl]phosphonic acid.

In a more preferred embodiment of the present invention, the compound used for treating pain is [2-(8,9-Dioxo-2,6-diazabicyclo[5.2.0]non-1(7)-en-2-yl)ethyl]phosphonic acid, having the formula:

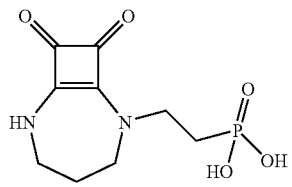

or a pharmaceutically acceptable salt form thereof.

While in no way intending to be bound in theory, it is believed that the cyclobutene derivatives of the present invention have a unique affinity and selectivity for certain binding sites on the NMDA receptor. This unique affinity and selectivity is believed to provide effective treatment of pain at lower doses and/or cause less side effects at doses needed to relieve pain.

The cyclobutene derivatives described herein are useful for treating pain in mammals in accordance with the methods of the present invention. By "treating", as used herein, it is meant partially or completely alleviating, inhibiting, ameliorating and/or relieving pain. For example, "treating" as used herein includes partially or completely alleviating, inhibiting or relieving pain for a period of time. "Treating" also includes completely ameliorating the pain.

The compounds useful in the present invention are useful for treating a variety of different types of pains experienced by mammals, such as humans. For example, the compounds of the present invention are effective in treating acute pain (short duration) or chronic pain (regularly reoccurring or persistent). This pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a preferred embodiment, the compounds useful in this invention are used to treat chronic pain that is neuropathic pain, visceral pain, musculoskeletal pain, bony pain, headache, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, postherpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The cyclobutene derivatives useful in the present invention can be administered in a variety of ways including for example by oral, intramuscular, intraperitoneal, epidural, intrathecal, intravenous, subcutaneous, intramucosal such as sublingual or intranasal, or transdermal administration. In a preferred embodiment of the present invention, the compounds useful in the present invention are administered orally, intramucosally or intravenously.

The compounds useful in the present invention are administered in a pain treating effective amount to the mammal needing treatment for pain. As used herein "a pain treating effective amount" is at least the minimal amount of the cyclobutene derivative or a pharmaceutically acceptable salt form thereof, which treats the pain in question. To determine the pain treating effective amount of the compound to be administered in the treatment of pain, the physician may, for example, evaluate the effects of a given cyclobutene derivative in the patient by incrementally increasing the dosage, such as an oral dosage, preferably from about 3 mg/kg to about 1000 mg/kg until the desired symptomatic relief level is achieved. The continuing-dose regimen may then be modified to achieve the desired result, with the range for oral dosage being preferably from about 150 mg/day to about 900 mg/day. Similar techniques may be followed by determining the effective dose range for other administration routes such as by intravenous or intramuscular routes based on bioavailability data. For example, it is estimated that intravenous dosages would preferably range from about 3 mg/day to about 50 mg/day.

Although the cyclobutene derivatives may be administered in accordance with the methods of the present invention as the sole active ingredient for treating pain, the present inventors have found that the cyclobutene derivatives may also be administered with one or more other pain relieving agents. By "pain relieving agents" it is meant any agent that directly or indirectly treats pain symptoms. Examples of indirect pain relieving agents include for example anti-inflammatory agents, such as anti-rheumatoid agents.

The one or more other pain relieving agents may be administered simultaneously (such as individually at the same time, or together in a pharmaceutical composition), and/or successively with one or more cyclobutene derivatives useful in the present invention. Preferably, the cyclobutene derivative and the one or more pain relieving agents are administered in a manner so that both are present in the mammal body for a certain period of time to treat pain.

The method of administration of the other pain relieving agent may be the same or different from the route of administration used for the cyclobutene derivative. For example, the other pain relieving agent may be administered by oral, intramuscular, intraperitoneal, epidural, intrathecal, intravenous, intramucosal such as by intranasal or sublingual, subcutaneous or transdermal administration. The preferred administration route will depend upon the particular pain relieving agent chosen and its recommended administration route(s) known to those skilled in the art. For example, opioids are preferably administered by oral, intravenous, or intramuscular administration routes.

One skilled in the art will recognize that the dosage of the other pain relieving agent administered to the mammal will depend on the particular pain relieving agent in question and the desired administration route. Accordingly, the other pain relieving agent may be dosed and administered according to those practices known to those skilled in the art such as those disclosed in references such as the Physicians' Desk Reference, 55 Edition, 2001, published by Medical Economics Co., Inc., Montvale, N.J.

Examples of pain relieving agents that may be administered with the cyclobutene derivatives useful in the present invention include analgesics such as non-narcotic analgesics or narcotic analgesics; anti-inflammatory agents such as non-steroidal anti-inflammatory agents (NSAID), steroids or anti-rheumatic agents; migraine preparations such as beta adrenergic blocking agents, ergot derivatives, or isometheptene; tricyclic antidepressants such as amitryptyline, desipramine, or imipramine; anti-epileptics such as gabapentin, carbamazepine, topiramate, sodium valproate or phenyloin; $\alpha_2$ agonists; or selective serotonin reuptake inhibitors/selective norepinepherine uptake inhibitors, or combinations thereof. One skilled in the art will recognize that some agents described hereinafter act to relieve multiple conditions such as pain and inflammation, while other agents may just relieve one symptom such as pain. A specific example of an agent having multiple properties is aspirin, where aspirin is anti-inflammatory when given in high doses, but at lower doses is just an analgesic. The pain relieving agent may include any combination of the aforementioned agents, for example, the pain relieving agent may be a non-narcotic analgesic in combination with a narcotic analgesic.

Non-narcotic analgesics useful in the present invention include, for example, salicylates such as aspirin, ibuprofen (MOTRIN®, ADVIL®, ketoprofen (ORUDIS®), naproxen (NAPROSYN®), acetaminophen, indomethacin or combinations thereof. Examples of narcotic analgesic agents that may be used in combination with the cyclobutene derivatives include opioid analgesics such as fentenyl, sufentanil, morphine, hydromorphone, codeine, oxycodone, buprenorphine or pharmaceutically acceptable salts thereof or combinations thereof. Examples of anti-inflammatory agents that may be used in combination with the cyclobutene derivatives include but are not limited to aspirin; ibuprofen; ketoprofen; naproxen; etodolac (LODINE®); COX-2 inhibitors such as celecoxib (CELEBREX®), rofecoxib (VIOXX®), valdecoxib (BEXTRA®), parecoxib, etoricoxib (MK663), deracoxib, 2-(4-ethoxy-phenyl)-3-(4-methanesulfonyl-phenyl)-pyrazolo[1,5-b]pyridazine, 4-(2-oxo-3-phenyl-2,3-dihydrooxazol-4-yl)benzenesulfonamide, darbufelone, flosulide, 4-(4-cyclohexyl-2-methyl-5-oxazolyl)-2-fluorobenzenesulfonamide), meloxicam, nimesulide, 1-Methylsulfonyl-4-(1,1-dimethyl-4-(4-fluorophenyl)cyclopenta-2,4-dien-3-yl)benzene, 4-(1,5-Dihydro-6-fluoro-7-methoxy-3-(trifluoromethyl)-(2)-benzothiopyrano(4,3-c)pyrazol-1-yl)benzenesulfonamide, 4,4-dimethyl-2-phenyl-3-(4-methylsulfonyl)phenyl)cyclo-butenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropyl butan-1-one, or their physiologically acceptable salts, esters or solvates; sulindac (CLINORIL®); diclofenac (VOLTAREN®); piroxicam (FELDENE®); diflunisal (DOLOBID®), nabumetone (RELAFEN®), oxaprozin (DAYPRO®), indomethacin (INDOCIN®); or steroids such as PEDIAPED® prednisolone sodium phosphate oral solution, SOLU-MEDROL® methylprednisolone sodium succinate for injection, PRELONE® brand prednisolone syrup.

Further examples of anti-inflammatory agents preferably used for treating rheumatoid arthritis include naproxen, which is commercially available in the form of EC-NAPROSYN® delayed release tablets, NAPROSYN®, ANAPROX® and ANAPROX® DS tablets and NAPROSYN® suspension from Roche Labs, CELEBREX® brand of celecoxib tablets, VIOXX® brand of rofecoxib, CELESTONE® brand of betamethasone, CUPRAMINE® brand penicillamine capsules, DEPEN® brand titratable penicillamine tablets, DEPO-MEDROL brand of methylprednisolone acetate injectable suspension, ARAVA™ leflunomide tablets, AZULFIDIINE EN-tabs® brand of sulfasalazine delayed release tablets, FELDENE® brand piroxicam capsules, CATAFLAM® diclofenac potassium tablets, VOLTAREN® diclofenac sodium delayed release tablets, VOLTAREN®-XR diclofenac sodium extended release tablets, or ENBREL® etanerecept products.

Examples of other agents used to treat inflammations, especially rheumatoid arthritis include immunosuppressants such as GENGRAF™ brand cyclosporine capsules, NEORAL® brand cyclosporine capsules or oral solution, or IMURAN® brand azathioprine tablets or IV injection; INDOCIN® brand indomethacin capsules, oral suspension or suppositories; PLAQUENIL® brand hydroxychloroquine sulfate; or REMICADE® infliximab recombinant for IV injection; or gold compounds such as auranofin or MYOCHRISYINE® gold sodium thiomalate injection.

The cyclobutene derivatives useful in the present invention may also be administered with one or more other pharmaceutical active agents such as those agents being used to treat any other medical condition present in the mammal that is related or unrelated to the pain being experienced by the mammal. Examples of such pharmaceutical active agents include antiangiogenic agents, anti-neoplastic agents, anti-diabetic agents, anti-infective agents, or gastrointestinal agents, or combinations thereof.

A more complete listing of pharmaceutical active agents, including pain relieving agents, can be found in the Physicians' Desk Reference, 55 Edition, 2001, published by Medical Economics Co., Inc., Montvale, N.J. Each of these agents may be administered according to the pharmaceutically effective dosages and regimens known in the art, such as those described for the products in the Physicians' Desk Reference, 55 Edition, 2001, published by Medical Economics Co., Inc., Montvale, N.J.

In a preferred embodiment of the present invention, at least one cyclobutene derivative is administered with at least one opioid analgesic in accordance with the methods previously described herein. It has surprisingly been found that the cyclobutene derivatives useful in the present invention, when administered with at least one opioid analgesic such as morphine, have such beneficial effects as synergistically decreasing pain perception, increasing the duration of pain relief, and/or decreasing adverse side effects to a greater extent than other comparitor NMDA antagonists.

The cyclobutene derivatives useful in the present invention may be administered neat (i.e., as is) or in a pharmaceutical composition. Pharmaceutical compositions useful in the present invention may be in any form known to those skilled in the art such as in liquid or solid form.

Pharmaceutical compositions, in addition to containing a pain treating effective amount of one or more cyclobutene derivatives of the present invention, may include one or more ingredients known to those skilled in the art for formulating pharmaceutical compositions. Such ingredients include for example, carriers (e.g., in solid or liquid form), flavoring agents, lubricants, solubilizers, suspending agents, fillers, glidants, compression aids, binders, tablet-disintegrating agents, encapsulating materials, emulsifiers, buffers, preservatives, sweeteners, thickening agents, coloring agents, viscosity regulators, stabilizers or osmo-regulators, or combinations thereof.

Solid pharmaceutical compositions preferably contain one or more solid carriers, and optionally one or more other additives such as flavoring agents, lubricants, solubilizers, suspending agents, fillers, glidants, compression aids, binders or tablet-disintegrating agents or an encapsulating material. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes or ion exchange resins, or combinations thereof. In powder pharmaceutical compositions, the carrier is preferably a finely divided solid which is in admixture with the finely divided active ingredient. In tablets, the active ingredient is mixed with a carrier having the necessary compression properties in suitable proportions, and optionally, other additives, and compacted into the desired shape and size. Solid pharmaceutical compositions, such as powders and tablets, preferably contain up to 99% of the active ingredient.

Liquid pharmaceutical compositions preferably contain one or more cyclobutene derivatives and one or more liquid carriers to form solutions, suspensions, emulsions, syrups, elixirs, or pressurized compositions. Pharmaceutically acceptable liquid carriers include for example water, organic solvent, pharmaceutically acceptable oils or fat, or combinations thereof. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators, or combinations thereof.

Examples of liquid carriers suitable for oral or parenteral administration include water (preferably containing additives such as cellulose derivatives such as sodium carboxymethyl cellulose), alcohols or their derivatives (including monohydric alcohols or polyhydric alcohols such as glycols) or oils (e.g., fractionated coconut oil and arachis oil). For parenteral administration the carrier can also be an oily ester such as ethyl oleate and isopropyl myristate. The liquid carrier for pressurized compositions can be halogenated hydrocarbons or other pharmaceutically acceptable propellant.

Liquid pharmaceutical compositions which are sterile solutions or suspensions can be administered parenterally, for example by, intramuscular, intraperitoneal, epidural, intrathecal, intravenous or subcutaneous injection. Pharmaceutical compositions for oral or transmucosal administration may be either in liquid or solid composition form.

In a preferred embodiment of the present invention, the pharmaceutical composition, in addition to containing the cyclobutene derivative may also contain a pharmaceutically effective amount of one or more pain relieving agents as previously described herein, and/or a pharmaceutically effective amount one or more other pharmaceutical active agents as previously described herein. Thus, the present invention also provides a pharmaceutical composition for treating pain containing a pain treating effective amount of at least one cyclobutene derivative useful in the present invention and a pharmaceutically effective amount of at least one pain relieving agent as previously described. In a more preferred embodiment, the pain relieving agent includes an opioid analgesic.

Preferably the pharmaceutical composition is in unit dosage form, such as tablets or capsules. In such form, the composition is sub-divided in unit dose containing appropriate quantities of the active ingredient. The unit dosage forms can be packaged compositions, for example packeted powders, vials, ampoules, pre-filled syringes or sachets containing liquids. The unit dosage form can be, for example, a capsule or tablet itself, or it can be the appropriate number of any such compositions in package form.

Thus, the present invention also provides a pharmaceutical composition in unit dosage form for treating pain in a mammal that contains a pain treating effective unit dosage of at least one cyclobutene derivative of the present invention. As one skilled in the art will recognize, the preferred pain treating effective unit dosage will depend on for example the method of administration. For example, a unit dosage for oral administration preferably ranges from about 75 mg to about 300 mg and more preferably from about 100 mg to about 300 mg of the cyclobutene derivative useful in the present invention.

The present invention also provides a therapeutic package for dispensing the cyclobutene derivative useful in the present invention to a mammal being treated for pain. Preferably, the therapeutic package contains one or more unit dosages of the cyclobutene derivative and a container containing the one or more unit dosages and labeling directing the use of the package for treating pain in a mammal. In a preferred embodiment, the unit dose is in tablet or capsule form. In a preferred embodiment, each unit dosage is a pain treating effective amount.

EXAMPLES

The cyclobutene derivatives useful in the present invention were evaluated for their effectiveness to treat pain. NMDA receptor antagonists known to relieve pain were also tested for comparison.

The test methods used herein have been used by others skilled in the art to evaluate the effectiveness of compounds for relieving pain. See e.g., Bennett G J and Xie T K, *A peripheral mononeuropathy in rat produces disorders of pain sensation like those seen in man*, Pain 33: 87-107 (1988); Chaplan S R, Bach R W, Pogrel J W, Chung J M and Yaksh T L, *Quantitative assessment of tactile allodynia in the rat paw*, J. Neurosci. Methods 53: 55-63 (1994); and Mosconi T and Kruger L, *Fixed-diameter polyethylene cuffs applied to the rat sciatic nerve induce a painful neuropathy: ultrastructural morphometric analysis of axonal alterations* Pain 64: 37-57 (1996).

Subjects

Individually housed Sprague-Dawley rats had free access to rat chow and water. A 12-h light/12-h dark cycle was in effect (lights on from 6:00 am to 6:00 pm). Animal maintenance and research were conducted in accordance with the guidelines provided by the National Institutes of Health Committee on Laboratory Animal Resources. These subjects were used in the tests below.

Compounds Tested

The cyclobutene derivatives tested in the examples were:
A. [2-(8,9-Dioxo-2,6-diazabicyclo[5.2.0]non-1(7)-en-2-yl)ethyl]phosphonic acid (referred to as Compound A); and
B. 2-[(1H-Tetrazol-5-yl)methyl]-2,6-diazabicyclo[5.2.0]-non-1-(7)-ene-8,9-dione (referred to as Compound B).

Compounds A and B were produced according to synthesis methods described in U.S. Pat. No. 5,990,307 to Asselin and U.S. Pat. No. 5,168,103 to Kinney et al., respectively.

The cyclobutene derivatives of the present invention were compared to one or more of the following NMDA antagonists known for relieving pain:
memantine, obtained from RBI (Natick, Mass.)
dizocilipine, obtained from RBI (Natick, Mass.)
ketamine, obtained from Fort Dodge (Fort Dodge, IO)
ifenprodil, obtained from Sigma (St. Louis, Mo.)
CGS-19755, obtained from Tocris (Ellisville, Mo.)

Ketamine and dizocilpine are high affinity use-dependent NMDA receptor channel blockers, while memantine is a moderate affinity use-dependent NMDA receptor channel blocker. CGS-19755 is a competitive NMDA antagonist and ifenprodil is a competitive polyamine antagonist.

Test Method 1: Prostaglandin $E_2$-Induced Thermal Hypersensitivity.

The terminal 10 cm of the tail was placed into a thermos bottle containing water warmed to 38, 42, 46, 50, 54, or 58° C. The latency in seconds for the animal to remove the tail from the water was used as a measure of nociception. If the animal did not remove the tail within 20 sec, the experimenter removed the tail and a maximum latency of 20 sec was recorded.

Following the assessment of baseline thermal sensitivity, thermal hypersensitivity was produced by a 50 μL injection of 0.1 mg prostaglandin $E_2$ ($PGE_2$) into the terminal 1 cm of the tail. Temperature-effect curves were generated before (baseline) and after (15, 30, 60, 90 and 120 min) the $PGE_2$ injection. Previous studies in other species (e.g., monkeys; Brandt et al., *J. Pharmacol. Exper. Ther.* 296:939, 2001) and results from the current study demonstrate that $PGE_2$ produces a dose- and time-dependent thermal hypersensitivity that peaks 15 min after injection and dissipates after 2 hr.

Single compound studies. The ability of drugs to reverse $PGE_2$-induced thermal hypersensitivity was assessed using a single dose time-course procedure. Under this procedure, a single dose of the compound to be tested was administered intraperitoneally (IP), orally (PO) or intranasally (IN) 30 min before the injection of $PGE_2$. Tactile sensitivity was assessed 30 min after $PGE_2$ injection.

Combination compound studies. Combination studies with NMDA receptor antagonists together with the mu opioid agonist morphine were conducted. A minimally effective dose of morphine (5.6 mg/kg) was administered alone and in combination with ineffective doses of NMDA receptor antagonists in the thermal warm-water tail withdrawal assay. Compounds were administered IP at the same time 30 min before testing.

Combination studies with NMDA receptor antagonists together with the mu opioid agonist morphine were also conducted in the $PGE_2$-induced thermal hypersensitivity assay. A dose of morphine (5.6 mg/kg) that completely reversed thermal hypersensitivity (i.e., return to baseline) was administered alone and in combination with doses of NMDA receptor antagonists in the PGE$_2$-induced thermal warm-water tail withdrawal assay. Compounds were administered IP at the same time as PGE$_2$, which was administered 30 min before testing.

Test Method 1 Data Analysis—The temperature that produced a half-maximal increase in the tail-withdrawal latency (i.e., T$_{10}$) was calculated from each temperature-effect curve. The T$_{10}$ was determined by interpolation from a line drawn between the point above and the point below 10 sec on the temperature-effect curve. For these studies, thermal hypersensitivity was defined as a leftward shift in the temperature-effect curve and a decrease in the T$_{10}$ value. Reversal of thermal hypersensitivity was defined as a return to baseline of the temperature-effect curve and the T$_{10}$ value and was calculated according to the following equation:

$$\% MPE \frac{(T_{10}^{drug+PGE2}) - (T_{10}^{PGE2})}{(T_{10}^{baseline}) - (T_{10}^{PGE2})} \times 100$$

in which T$_{10}^{drug+PGE2}$ is the T$_{10}$ after a drug in combination with PGE$_2$, T$_{10}^{PGE2}$ is the T$_{10}$ after PGE$_2$ alone, and T$_{10}^{baseline}$ is the T$_{10}$ under control conditions. A % MPE value of 100 indicates a complete return to the baseline thermal sensitivity observed without the PGE$_2$ injection. A value of greater than 100% indicates that the compound tested reduced thermal sensitivity more than the baseline thermal sensitivity without the PGE$_2$ injection.

Test Method 2: Chronic Constriction Injury

Rats were anesthetized with 3.5% halothane in O$_2$ at 1 L/min and maintained with 1.5% halothane in O$_2$ during surgery. A modified chronic sciatic nerve constriction injury (Mosconi & Kruger, 1996; Bennett & Xie, 1988) was produced by a cutaneous incision and a blunt dissection through the biceps femoris to expose the sciatic nerve. A PE 90 Polyethylene tubing (Intramedic, Clay Adams; Becton Dickinson Co.) cuff (2 mm length) was placed around the sciatic nerve at the level of the mid-thigh. The wound was closed in layers using 4-0 silk suture and wound clips. Testing was conducted 6-10 days after surgery.

Animals were placed in elevated wire cages and allowed 45-60 minutes to acclimate to the testing room. Baseline tactile sensitivity was assessed using a series of calibrated von Frey monofilaments (Stoelting; Wood Dale, Ill.) 0-3 days before surgery. Von Frey monofilaments were applied to the mid-plantar hind paw in sequential ascending or descending order, as necessary, to hover as closely as possible to the threshold of responses. The threshold was indicated by the lowest force that evoked a brisk withdrawal response to the stimuli. Thus, a withdrawal response led to the presentation of the next lighter stimulus and the lack of a withdrawal response led to the presentation of the next stronger stimulus. Rats with baseline thresholds <10 g force were excluded from the study. Approximately one week following CCl surgery, tactile sensitivities were reassessed and animals that exhibited motor deficiency (i.e. paw dragging) or failure to exhibit subsequent tactile hypersensitivity (threshold ≧10 g) were excluded from further testing. Under cumulative dosing conditions, compounds were administered IP every 30 minutes with the cumulative dose increasing in ½ log unit increments. Tactile hypersensitivity was assessed 20-30 minutes following each drug administration.

Test Method 2 Data Analysis—The 50% threshold values (in gm force) estimated by the Dixon non-parametric test (Chaplan et al, 1994) was calculated and fifteen-grams of force was used as the maximal force. Dose-effect curves were generated for each experimental condition for each rat. Individual tactile hypersensitivity threshold values were averaged to provide a mean (±1 SEM). Reversal of tactile hypersensitivity was defined as a return to baseline tactile sensitivity and was calculated according to the following equation:

$$\% Reversal = \frac{(50\%^{drug+CCl}) - (50\%^{CCl})}{(50\%^{baseline}) - (50\%^{CCl})} \times 100$$

in which 50%$^{drug+CCl}$ is the 50% value after compound in animals approximately one week after CCl surgery, 50%$^{CCl}$ is the 50% value approximately one week after CCl surgery alone, and 50%$^{baseline}$ is the 50% value before CCl surgery. Maximal effect of 100% reversal represents a return to the mean pre-operative threshold value for subjects in that experimental condition.

Test Method 3: Scheduled-Controlled Responding.

Rats were trained under a multiple-cycle procedure during experimental sessions conducted five days each week. Each training cycle consisted of a 1-min pretreatment period followed by a 10-min response period. During the pretreatment period, stimulus lights were not illuminated, and responding had no scheduled consequences. During the response period, the left or right stimulus lights were illuminated (counterbalanced among subjects), the response lever was extended and subjects could respond under a fixed ratio 30 schedule of food presentation. Training sessions consisted of 3 consecutive cycles. Testing sessions were identical to training sessions except that a single dose of drug was administered at the start of the first cycle.

Data analysis. Operant response rates from individual animals were averaged for the three cycles during test sessions and were converted to percent of control response rates using the average rate from the previous training day as the control value (i.e., average of three cycles). Data are presented as the mean (±1 SEM) response rate as a percent of control. Thus, for example, a test value of 100% would indicate the response rate after administration of the compound to be tested was the same as the control response rate and there was no adverse effect of the compound tested.

Results

Test Method 1: Baseline Thermal Nociception and PGE$_2$-Induced Thermal Hypersensitivity.

Under baseline conditions, maximal tail-withdrawal latencies (i.e., 20 sec) were typically obtained with temperatures of 38, 42, and 46° C. When the water temperature was increased to 50° C., tail-withdrawal latencies for individual rats were typically between 5 and 15 sec. The highest temperature of 54° C. produced tail-withdrawal latencies below 10 sec in all rats. Average baseline T$_{10}$ values (withdrawal in 10 seconds) were between 49° C. and 51° C.

A dose of 0.1 mg PGE$_2$ produced a dose- and time-dependent thermal hypersensitivity manifested as a leftward shift in the temperature-effect curve and a decrease in the T$_{10}$ value. Maximal decreases in tail-withdrawal latencies occurred 15 min after administration, and latencies returned to baseline by 120 min after injection.

Table 1 below shows the effects of PGE$_2$ in combination with comparative NMDA antagonist compounds. Up to doses that produced observable signs of sedation and ataxia (i.e., Comp. Ex. 1-<10 mg/kg, Comp. Ex. 2-<100 mg/kg, Comp. Ex. 3-<0.3 mg/kg, Comp. Ex. 4 to 6-<30 mg/kg), none of the comparative compounds, including memantine (Comp. Example 1 and 2), dizocilpine (Comp. Example 3), ketamine (Comp. Example 4), ifenfrodil (Comp. Example 5) or CGS- 19755 (Comp. Example 6), produced greater than a 25% reversal of $PGE_2$-induced thermal hypersensitivity. In comparison, [2-(8,9-Dioxo-2,6-diazabicyclo[5.2.0]non-1(7)-en-2-yl)ethyl]phosphonic acid, a cyclobutene derivative useful in the present invention (Compound A), produced a 79% reversal following IP administration at 10 mg/kg and a 87% reversal following PO administration at 100 mg/kg. These doses (as high as 178 mg/kg) were not associated with sedation or ataxia as seen with the comparative compounds. In addition, 1 mg or 3 mg of Compound A administered intranasally (IN) produced a 37% or 79% reversal, respectively. The mean dose calculated from subject weight represents doses of 2.6 and 7.5 mg/kg, respectively. Similarly, another cyclobutene derivative useful in the present invention, 2-[(1H-Tetrazol-5-yl)methyl]-2,6-diazabicyclo[5.2.0]-non-1-(7)-ene-8,9-dione (Compound B) produced a full reversal of $PGE_2$-induced thermal hypersensitivity.

The effectiveness of the cyclobutene derivatives useful in the present invention, such as Compounds A and B, in relieving pain, such as thermal hypersensitivity, is surprising and unexpected. For example, all the compounds tested according to test method 1 were NMDA receptor antagonists, however Compounds A and B performed substantially and significantly better that the comparative compounds. It is especially important to note that both Compounds A and B, like the comparative compound CGS-19755 are competitive glutamate NMDA receptor antagonists, but Compounds A and B performed significantly and substantially better.

TABLE 1

Results of $PGE_2$-induced thermal hypersensitivity

| Example | Compound tested | Method of Admin. | % MPE Dose (mg/kg) | | | | | | |
|---|---|---|---|---|---|---|---|---|---|
| | | | 0.3 | 1 | 3 | 10 | 18 | 30 | 100 |
| Comp. Ex. 1 | memantine | IP | | | 13% | 15% | | | |
| Comp. Ex. 2 | memantine | PO | | | | -1% | | 11% | 5% |
| Comp. Ex. 3 | dizocilpine | IP | 18% | | | | | | |
| Comp. Ex. 4 | ketamine | IP | | | | 14% | 9% | | |
| Comp. Ex. 5 | ifenfrodil | IP | | | | 1% | | 14% | |
| Comp. Ex. 6 | CGS-19755 | IP | | | 9% | 25% | | 9% | |
| Example 7 | A | IP | | -7% | 66% | 79% | | | |
| Example 8 | A | PO | | | | 5% | | 23% | 87% |
| Example 9 | A | IN | | 37%* | 79%** | | | | |
| Example 10 | B | PO | | | 16% | 92% | | 101% | |

*displayed in column for approximation; actual mean dose is 2.6 mg/kg
**displayed in column for approximation; actual mean dose is 7.5 mg/kg The cyclobutene derivatives useful in the present invention were also tested with an opioid analgesic to determine the ability of the cyclobutene derivative to reduce thermal sensitivity in combination with an opioid analgesic, morphine. A minimally effective dose of morphine was administered alone and in combination with ineffective doses of the compounds to be tested. Table 1-2 shows examples in the warm-water tail withdrawal assay. A dose of 5.6 mg/kg morphine IP (Comp. Ex 11) produced a small yet significant increase in the $T_{10}$ (51.2±0.7) compared to the vehicle $T_{10}$ (48.9±0.1). When administered in combination with 5.6 mg/kg morphine, an ineffective dose of 18 mg/kg ketamine IP (Comp. Ex. 12) produced a non-significant increase in the $T_{10}$ (52.8±0.5) compared to morphine alone (Comp. Ex. 13). In contrast, an ineffective dose of 10 mg/kg Compound A IP (Ex 14) in combination with morphine significantly and surprisingly increased the $T_{10}$ (55.8±1.3) compared to morphine alone (Ex. 15).

TABLE 1-2

Warm-water tail withdrawal combination studies

| Example | Compound Tested | Dose (mg/kg) | Change from Baseline |
|---|---|---|---|
| Comp. Ex. 11 | Morphine | 5.6 | +2.3 |
| Comp. Ex. 12 | Ketamine | 18.0 | -0.3 |
| Comp. Ex. 13 | Morphine + Ketamine | 5.6 + 18.0 | +3.9 |
| Ex. 14 | A | 10.0 | -0.3 |
| Ex. 15 | Morphine + A | 5.6 + 10.0 | +6.9 |

The cyclobutene derivatives useful in the present invention were also tested with an opioid analgesic to determine the ability of the cyclobutene derivative to reduce $PGE_2$-induced thermal hypersensitivity in combination with an opioid analgesic, morphine. Table 1-3 shows examples in the $PGE_2$-induced thermal hypersensitivity assay. $PGE_2$ injected into the tail significantly decreased the $T_{10}$ (44.8±0.1) compared to the vehicle $T_{10}$ (50.3±0.4; Comp. Ex. 16). A dose of 5.6 mg/kg morphine (Comp. Ex. 17) significantly reversed the $T_{10}$ to a value similar to vehicle (50.6±0.5). When administered in combination with 5.6 mg/kg morphine, an ineffective dose of 18 mg/kg Example 3 IP (Comp. Ex. 18) produced a non-significant increase in the $T_{10}$ (51.7±0.2) compared to morphine alone (Comp. Ex. 19). In contrast, an effective dose of 10 mg/kg Example 6 IP ($T_{10}$=48.8±0.2; Ex. 20) in combination with morphine significantly and surprisingly increased the $T_{10}$ (55.3±0.2) compared to morphine alone (Ex. 21).

TABLE 1-3

$PGE_2$-induced thermal hypersensitivity combination studies

| Example | Compound Tested | Dose (mg/kg) | Change from Baseline |
|---|---|---|---|
| Comp. Ex. 16 | vehicle | | -5.6 |
| Comp. Ex. 17 | Morphine | 5.6 | +0.3 |
| Comp. Ex. 18 | Ketamine | 18.0 | -5.5 |
| Comp. Ex. 19 | Morphine + Ketamine | 5.6 + 18.0 | +1.4 |
| Ex. 20 | A | 10.0 | -1.5 |
| Ex. 21 | Morphine + A | 5.6 + 10.0 | +5.0 |

Test Method 2 Results: Chronic Constriction Injury

Table 2 shows the effects of the cyclobutene derivatives useful in the present invention to reverse CCl-induced tactile hypersensitivity in animals that had received CCl surgery one week before testing. NMDA receptor antagonists memantine (Comp. Ex 22) and CGS-19755 (Comp. Ex 23) were also tested for comparison. Up to doses that produced observable signs of sedation and ataxia (i.e., Comp. Ex. 22-<10 mg/kg, Comp. Ex. 23-<30 mg/kg), none of the comparative compounds produced any reversal of CCl-induced tactile hypersensitivity. In comparison, Compound A (Example 24) produced a 97% reversal following IP administration and Compound B (Example 25) produced a 40% reversal following IP administration. The doses for compounds A and B were not associated with sedation or ataxia as was seen with the comparative compounds.

TABLE 2

Chronic Constriction Injury-induced tactile hypersensitivity

| Example | Compound tested | Method of Admin. | % Reversal Dose (mg/kg) | | | |
|---|---|---|---|---|---|---|
| | | | 1 | 3 | 10 | 30 |
| Comp. Ex. 22 | memantine | IP | | | −25% | −45% |
| Comp. Ex. 23 | CGS-19755 | IP | | −9% | −5% | −17% |
| Example 24 | A | IP | 13% | 45% | 97% | |
| Example 25 | B | IP | 13% | 14% | 40% | 12% |

The effectiveness of the cyclobutene derivatives useful in the present invention, such as Compounds A and B, in relieving pain, such as CCl-induced tactile hypersensitivity, is surprising and unexpected. For example, Compounds A and B performed significantly and substantially better than known NMDA receptor antagonists memantine and CGS-19755.

Test Method 3 Results

To assess potential adverse effects of the cyclobutene derivatives useful in the present invention, Compound A was administered to animals responding under a schedule of food presentation. NMDA receptor antagonists memantine and dizocilpine were also tested for comparison. Table 3 shows that memantine (Comp. Ex. 26) and dizocilpine dose-dependently decreased rates of responding. These were doses that also did not reverse $PGE_2$-induced thermal hypersensitivity or CCl-induced tactile hypersensitivity. In contrast, Compound A administered IP (Example 28) or PO (Example 29), unexpectedly did not significantly modify rates of responding at doses that reversed $PGE_2$-induced thermal hypersensitivity or CCl-induced tactile hypersensitivity.

TABLE 3

| Example | Compound Tested | Method of Admin. | Operant responding Dose (mg/kg) | | | | | |
|---|---|---|---|---|---|---|---|---|
| | | | 0.1 | 0.3 | 3 | 10 | 30 | 100 |
| Comp. Ex. 26 | memantine | IP | | | | 93% | 2% | |
| Comp. Ex. 27 | dizocilpine | IP | 63% | 16% | | | | |
| Example 28 | A | IP | | | | 111% | 86% | |
| Example 29 | A | PO | | | | 112% | 97% | 100% |

What is claimed:

1. A pharmaceutical composition comprising:

a) an effective amount of at least one compound of formula (I):

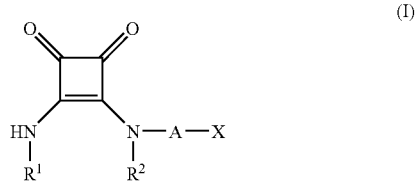

wherein:

$R^1$ is hydrogen, alkyl of 1 to 6 carbon atoms or phenylalkyl of 7 to 12 carbon atoms;

$R^2$ is hydrogen, alkyl of 1 to 6 carbon atoms, alkenyl of 2 to 6 carbon atoms or phenylalkyl of 7 to 12 carbon atoms; or $R^1$ and $R^2$ taken together as Z are $-CH_2CH_2-$, $-CH_2C(R^6)(R^7)CH_2-$ or $-CH_2C(R^8)(R^9)-C(R^{10})(R^{11})CH_2-$, where $R^6$, $R^8$ and $R^{10}$ are, independently, hydrogen, alkyl of 1 to 6 carbon atoms or hydroxyl and $R^7$, $R^9$ and $R^{11}$ are, independently, hydrogen or alkyl of 1 to 6 carbon atoms;

A is alkylene of 1 to 6 carbon atoms or alkenylene of 2 to 6 carbon atoms;

X is $CO_2R^3$, $P(O)(OR^4)(OR^5)$, 3,5-dioxo-1,2,4-oxadiazolidin-2-yl or 5-tetrazolyl wherein $R^3$, $R^4$ and $R^5$ are, independently, hydrogen or alkyl of 1 to 6 carbon atoms;

or a pharmaceutically acceptable salt thereof; and b) a pharmaceutically effective amount of at least one pain relieving agent.

2. The composition of claim 1 wherein the compound of formula (I) is a compound of formula (III):

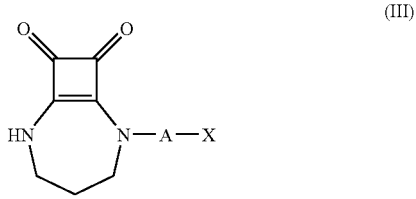

wherein A and X are defined as in claim 1.

3. The composition of claim 1 wherein the compound of formula (I) comprises at least one of:

[2-(7,8-Dioxo-2,5-diazabicyclo[4.2.0]oct-1(6)-en-2-yl)ethyl]phosphonic acid,

[2-(8,9-Dioxo-2,6-diazabicyclo[5.2.0]non-1(7)-en-2-yl)ethyl]phosphonic acid,

[2-(4-Hydroxy-8,9-dioxo-2,6-diazabicyclo-[5.2.0]non-1(7)en-2-yl)ethyl]phosphonic acid, 8,9-Dioxo-2,6-diazabicyclo[5.2.0]non-1(7)-ene-2-acetic acid, 2-[(1H-Tetrazol-5-yl)methyl]-2,6-diazabicyclo[5.2.0]-non-1-(7)-ene-8,9-dione, or

[2-(9,10-Dioxo-2,7-diazabicyclo[6.2.0]dec-1(8)-en-2-yl)ethyl]phosphonic acid; or a pharmaceutically acceptable salt form thereof.

4. The composition of claim 1 wherein the pain relieving agent comprises at least one opioid analgesic.

5. The composition of claim 1, wherein said effective amount of at least one compound of formula (I) is about 150 mg to about 900 mg.

6. The composition of claim 1, wherein said effective amount of at least one compound of formula (I) is about 3 mg to about 50 mg.

* * * * *